US006997037B2

(12) United States Patent
Thurston

(10) Patent No.: US 6,997,037 B2
(45) Date of Patent: *Feb. 14, 2006

(54) DETERMINATION OF EFFECTIVE COMPOSITION OF A MIXTURE OF HYDROCARBON GASES

(75) Inventor: Robert R. Thurston, deceased, late of Melbourne (GB); by Loraine Thurston, legal representative, Melbourne (GB)

(73) Assignee: Lattice Intellectual Property, Ltd., London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/416,792

(22) PCT Filed: Nov. 12, 2001

(86) PCT No.: PCT/GB01/04992

§ 371 (c)(1),
(2), (4) Date: Aug. 16, 2004

(87) PCT Pub. No.: WO02/40992

PCT Pub. Date: May 23, 2002

(65) Prior Publication Data

US 2004/0261497 A1    Dec. 30, 2004

(30) Foreign Application Priority Data

Nov. 15, 2000   (GB) .................................... 0027875
May 29, 2001   (GB) .................................... 0112924

(51) Int. Cl.
G01N 25/00    (2006.01)

(52) U.S. Cl. ................... 73/23.2; 73/25.03; 73/25.01

(58) Field of Classification Search .................. 73/300, 73/23.2, 23.21, 25.01, 25.03
See application file for complete search history.

(56) References Cited

U.S. PATENT DOCUMENTS 4,520,654 A    6/1985   Terhune ......................... 73/24

(Continued)

FOREIGN PATENT DOCUMENTS

GB    2 210 977    6/1989

(Continued)

OTHER PUBLICATIONS

RM Lueptow et al.: "Acoustic sensor for determening combustion properties of natural gas" measurement Science and Technology, vol. 5, No. 11, pp. 1375-1381 Nov. 1, 1994.

(Continued)

*Primary Examiner*—Daniel S. Larkin
*Assistant Examiner*—Rodney Frank
(74) *Attorney, Agent, or Firm*—Oblon, Spivak, McClelland, Maier & Neustadt, P.C.

(57) ABSTRACT

A method and apparatus for determining the effective composition of a mixture of gases including a plurality of hydrocarbon gases, the method comprising selecting one or more effective hydrocarbons to represent the plurality of hydrocarbon gases in the gas mixture, the number of effective hydrocarbons being less than the number of hydrocarbon gases in the gas mixture whose composition is to be determined; measuring a number of characteristics of the gas mixture whose effective composition is to be determined, the number of characteristics to be measured being one less than the total number of components to be determined and determining the effective composition of the mixture of gases from the measurements of the characteristics of the gas mixture, a predetermined parameter dependent upon the characteristic measured and knowing that the sum of the components of the gas mixture equals 100%.

21 Claims, 2 Drawing Sheets

U.S. PATENT DOCUMENTS

| | | | | |
|---|---|---|---|---|
| 4,555,931 A | * | 12/1985 | Amimoto et al. | 73/23.2 |
| 5,272,907 A | * | 12/1993 | Hakala | 73/23.2 |
| 5,569,838 A | * | 10/1996 | Broedel et al. | 73/23.31 |

FOREIGN PATENT DOCUMENTS

| | | |
|---|---|---|
| GB | 2 312 508 | 10/1997 |
| GB | 2 333 370 | 7/1999 |
| GB | 2 333 371 | 7/1999 |
| WO | 00 19176 | 4/2000 |

OTHER PUBLICATIONS

R.W. Dawson et al.: "A technique for determining instantaneous N2, CO2, O2 and H2O species concentrations using multiplex CARS in premixed gaseous flames"Acerc Abstracts 6-96-PO2/Proceedings at the Fall Meeting of the Western States Section/Combustion Institute, No. 6-96-PO2, Oct. 28-29, 1996 retrieved from the internet: <URL:http://www-acerc.byu-edu/Abstracts/1996/1996-6.html>, on Jan. 17, 2002.

* cited by examiner

DETERMINATION OF EFFECTIVE COMPOSITION OF A MIXTURE OF HYDROCARBON GASES

The present invention relates to the determination of an effective composition of a mixture of hydrocarbon gases such as natural gas. The effective composition can be used to determine a quantity indicative of the quality of the gas such as its calorific value, relative density and Wobbe index.

Conventionally to determine the quality of a gas mixture such as its calorific value one could determine the proportion of each of the gases in the mixture and calculate the calorific value. However, for a mixture of several gases such as natural gas it is difficult to determine the proportion of each and every gas.

According to a first aspect of the present invention a method of determining an effective composition of a mixture of hydrocarbon gases comprises representing a mixture of hydrocarbon gases by an effective mixture of fewer hydrocarbon gases and determining the effective proportion of each of the hydrocarbon gases in the effective mixture.

The effective proportions of each of the hydrocarbon gases in the effective mixture is preferably used to determine a parameter indicative of the quality of the gas such as calorific value(CV), relative density (RD) or Wobbe index (WI).

An example of the invention will now be described with reference to the accompanying drawings in which.

Figure 1:
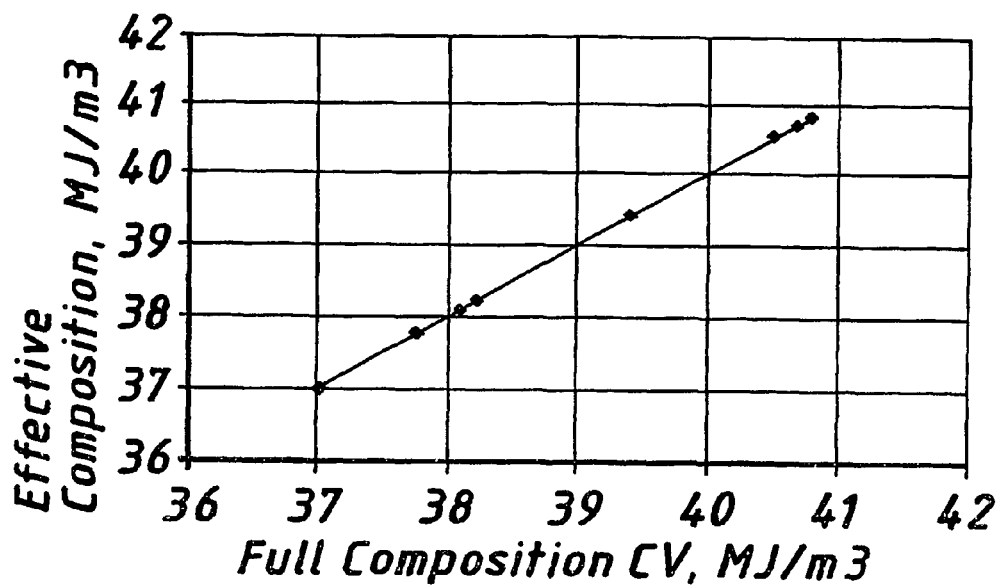
FIG. 1 shows CV determined in accordance with the present invention compared to actual values.

It has been found that a mixture of hydrocarbon gases such as natural gas can be represented by a reduced number of components. For example the many hydrocarbons in a natural gas can be represented by one or an effective mixture of two or more hydrocarbons. In the following example the hydrocarbons in a natural gas are represented by a mixture of effective methane ($CH_4$) and propane ($C_3H_8$). The proportions of the individual components of the effective gas are selected to produce the same major properties as the gas itself. The effective gas for the other hydrocarbons is the volume of propane and methane that has the same ideal volume and the same average number of carbon atoms per molecule as the gas under consideration. For example, consider ethane:

$$2C_2H_6 = C_3H_8 + CH_4$$

Ethane is represented in the effective gas by half its volume of propane and half its volume of methane. The effective factors for ethane in terms of propane and of methane are therefore, 0.5 and 0.5. Other hydrocarbons can be represented in these terms and their effective factors are tabulated below:

|  | Effective | |
| --- | --- | --- |
| Hydrocarbon | $CH_4'$ | $C_3H_8'$ |
| Methane | 1.0 | — |
| Ethane | 0.5 | 0.5 |
| Propane | — | 1.0 |
| Butane | −0.5 | 1.5 |
| Pentane | −1.0 | 2.0 |
| Hexane | −1.5 | 2.5 |

Natural gas generally also contains $CO_2$ and $N_2$ and so, assuming that the hydrocarbons are represented by an effective mix of methane and propane, the natural gas can be represented by a four component mixture of methane, propane, $CO_2$ and $N_2$. If the hydrocarbons are represented by just one hydrocarbon then the natural gas could be represented by an effective three component mix of the effective hydrocarbon, $CO_2$ and $N_2$.

An example is given below of a natural gas represented as an effective four component mixture of methane, propane, $CO_2$ and $N_2$. The actual composition of a sample of natural gas identified as bottle 2912 is as follows:

| Bottle ID | $CH_4$ % mol | $C_2H_6$ % mol | $C_3H_8$ % mol | N—$C_4H_{10}$ % mol | I—$C_4H_{10}$ % mol | N—$C_5H_{12}$ % mol | $CO_2$ % mol | $N_2$ % mol | CV MJ/m³ |
| --- | --- | --- | --- | --- | --- | --- | --- | --- | --- |
| 2912 | 94.451 | 3.11 | 0.512 | 0.109 | 0.089 | 0.170 | 0.647 | 0.912 | 38.73 |

Applying effective methane and propane calculations to the hydrocarbon samples of the above natural gas sample gives the following result:

| Hydrocarbon | | | $CH_4'$ | | | $C_3H_8'$ |
| --- | --- | --- | --- | --- | --- | --- |
| Methane | 1.0 | 94.451 | 94.451 | — | 94.451 | 0 |
| Ethane | 0.5 | 3.110 | 1.555 | 0.5 | 3.110 | 1.555 |
| Propane | — | 0.512 | 0 | 1.0 | 0.512 | 0.512 |
| Butane | −0.5 | 0.198 | −0.099 | 1.5 | 0.198 | 0.297 |
| Pentane | −1.0 | 0.170 | −0.170 | 2.0 | 0.170 | 0.340 |
| Hexane | −1.5 | 0 | 0 | 2.5 | 0 | 0 |
| | | $CH_4'$ = | 95.737 | | $C_3H_8'$ = | 2.704 |

Thus the hydrocarbons of the natural gas sample can be represented by an effective mixture of 95.737% methane and 2.704% propane. The $CO_2$ and $N_2$ samples can be included to provide the four component effective natural gas mixtures:

| Bottle ID | CH$_4$' % mol | C$_3$H$_8$' % mol | CO$_2$ % mol | N$_2$ % mol | Σ % mol |
| --- | --- | --- | --- | --- | --- |
| 2912 | 95.737 | 2.704 | 0.647 | 0.912 | 100 |

A Method has been found to determine the effective methane, propane, CO$_2$ and N$_2$ proportions in a sample of natural gas. It is known that the sum of the four components equals 100%. By making three measurements of the characteristics of the natural gas and knowing that the sum of the four components equals 100% the relative effective proportions of methane, propane, CO$_2$ and N$_2$ can be determined using simultaneous equations as shown below:

$$X = C1 \cdot CH_4 + C2 \cdot C_3H_8 + C3 \cdot CO_2 + C4 \cdot N_2$$

$$Y = C5 \cdot CH_4 + C6 \cdot C_3H_8 + C7 \cdot CO_2 + C8 \cdot N_2$$

$$Z = C9 \cdot CH_4 + C10 \cdot C_3H_8 + C11 \cdot CO_2 + C12 \cdot N_2$$

$$100 = CH_4\% + C_3H_8\% + CO_2\% + N_2\%$$

X, Y and Z are measurements taken of the sample of gas being investigated. In this case X is the thermal conductivity of the gas at a first temperature (THCst), Y is the thermal conductivity of the gas at a second temperature (ThCr) and Z is the speed of sound in the gas (SOS). The thermal conductivities of the gas at the two temperatures and the speed of sound of the gas are measured using any suitable technique as is well known in the art. Any convenient characteristics of the gas may be measured and used as X, Y or Z. The parameters C1 to C12 are constant for a particular measurement apparatus, and a particular temperature and pressure and the particular characteristic being measured. The values for C1 to C12 may be found by calibrating a particular apparatus using a gas of known effective methane, effective propane, CO$_2$ and N$_2$ proportions.

To determine the coefficients C1 to C12 at a fixed temperature and pressure, a set of data is determined which maps values of X, Y and Z for the expected range in gas composition. Regression analysis is then used with the gas components as the X input range and parameter X as the Y input range, the resulting analysis gives C1 to C4 at this temperature and pressure. This process is repeated with parameter Y as the Y input to give C5 to C8 and again with parameter Z as the Y input to give C9 to C12. This gives C1 and C12 at a fixed temperature and pressure.

These coefficients are temperature and pressure dependent. So the whole process needs to be repeated for a range of temperatures and pressures covering the specified operating range. Once this is complete a mathematical model can be determined to predict C1 to C12 at any temperature and pressure in the specified range.

The effective proportions of methane, propane, CO$_2$ and N$_2$ may be determined from the measured gas characteristics (in this example two thermal conductivities at different temperatures and the speed of sound) using a matrix method as shown below:

$$\begin{pmatrix} C1 & C2 & C3 & C4 \\ C5 & C6 & C7 & C8 \\ C9 & C10 & C11 & C12 \\ 1 & 1 & 1 & 1 \end{pmatrix}^{-1} \begin{pmatrix} ThC_{st} \\ ThC_r \\ SOS \\ 100 \end{pmatrix} = \begin{pmatrix} CH_4' \\ C_3H_8' \\ CO_2 \\ N_2 \end{pmatrix}$$

Once the effective proportions of methane, ethane, CO$_2$ and nitrogen and are known, these can be used to determine the calorific value (CV), relative density (RD) and Wobbe Index (WI) as explained below.

The ideal gas superior calorific value (water vapour condensed) on a volumetric basis, for a combustion temperature $t_1$, of a mixture of known composition metered at a temperature $t_2$ and pressure $p_2$, can be calculated using:

$$\tilde{H}_s^o[t_1 \cdot V(t_2, p_2)] = \sum_{J=1}^{N} x_j \cdot \tilde{H}_j^o[t_1 \cdot V(t_2, p_2)]$$

Where:

$\tilde{H}_s^o$ $[t_1.V(t_2,p_2)]$ is the ideal superior caloric value on a volumetric basis of the mixture.

Xj if the mole fraction of component j determined from the earlier effective constituent analysis.

$\tilde{H}_j^o[t1,V(t2,p2)]$ is the ideal superior calorific value on a volumetric basis of component j.

In the UK, Metric Standard Conditions (MSC) are preferred:

P$_2$ is 101.325 kPa (1.01325 bar A)

$t_1 = t_2 = 15°$ C. (288.15K)

Calorific Values for methane and propane at metric standard conditions are known:

| Component | $\tilde{H}_j^o$ [15, V (15, 101.325)] |
| --- | --- |
| CH$_4$ | 37.706 |
| C$_3$H$_8$ | 93.940 |

Multiplying these values by the proportions of methane and propane determined earlier provides a value for $\tilde{H}_s^o[t_1,V(t_2,p_2)]$ The real-gas caloric value on a volumetric basis is calculated from the equation:

$$\tilde{H}_s[t_1 \cdot V(t_2, p_2)] = \frac{H_s^o[t_1, V(t_2, p_2)]}{Z_{mix}(t_2, p_2)}$$

Where:

$\tilde{H}_s$ $[t_1.V(t_2,p_2)]$ is the real-gas superior calorific value on a volumetric basis.

The compression factor $Z_{mix}$ at the metering conditions is calculated using:

$$Z_{mix}(t_2, p_2) = 1 - \left[\sum_{J=1}^{N} X_j \cdot \sqrt{b_j} \cdot \right]^2$$

Where $\sqrt{b_j}$ is the so-called summation factor which for methane is 0.0447 and for propane is 0.1338.

FIG. 1 shows the CV determined as above using the effective composition plotted on the y-axis and the actual CV along the x-axis.

The CV calculated for the effective composition is within +/−0.008 MJ/m³ (2 standard deviations) of the actual CV along the x-axis.

The relative density (RD) of a gas is calculated using the following:

$$d^o = \sum_{J=1}^{N} X_j \cdot \frac{M_j}{M_{air}}$$

Where:

$d^o$ is the relative density of the ideal gas $M_j$ is the molar mass of component j $M_{air}$ is the molar mass of dry air of standard composition (28.9626 kg.kmol⁻¹)

The relative density of the real gas is calculated from:

$$d(t, p) = \frac{d^o \cdot Z_{air}(t, p)}{Z_{mix}(t, p)}$$

Where:

d(t,p) is the relative density of the real gas $Z_{air}$ (t,p) is the compression factor of dry air of standard composition (MSC=0.99958)

The compression factor $Z_{mix}$ at the metering conditions is calculated using;

$$Z_{mix}(t, p) = 1 - [\sum_{J=1}^{N} X_j \cdot [b_j]^2$$

Where:

$\sqrt{b_j}$ is the so-called summation factor which for methane is 0.0447 and for propane is 0.1338.

Figure 2:
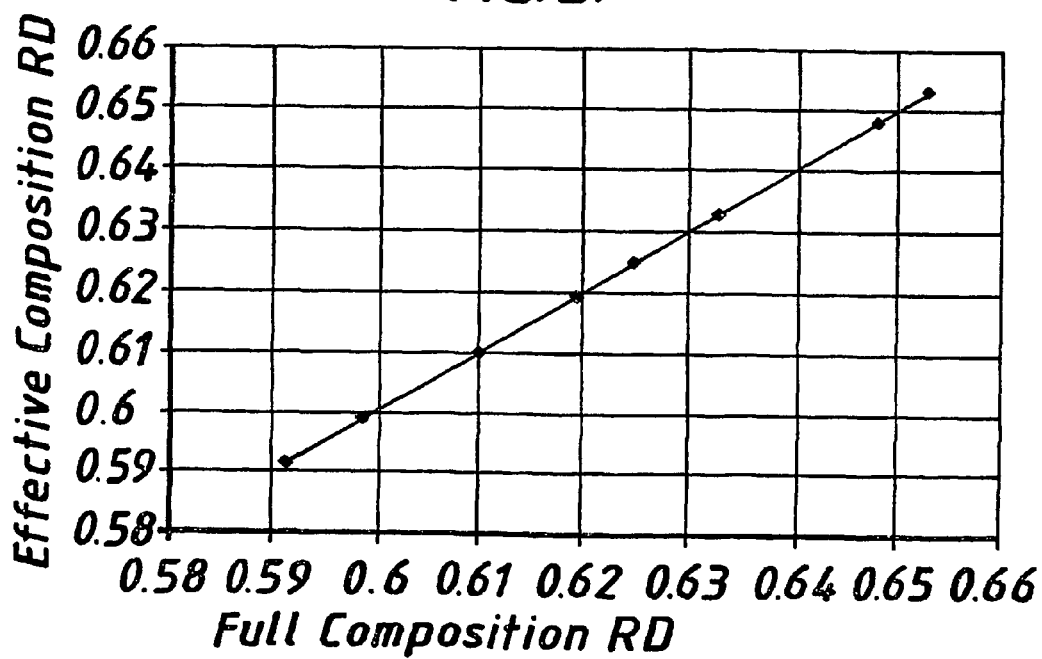
FIG. 2 shows RD determined in accordance with the present invention compared to actual values.

FIG. 2 shows the relative density determined assuming an effective composition of methane, propane, $CO_2$ and $N_2$ for various gas samples plotted on the y-axis and the actual relative density of those gas samples plotted on the x-axis.

The relative density calculated for the effective composition is within +/−0.00001 (2 standard deviations) of the actual values.

The Wobbe Index (WI) of a gas may be determined from the CV and RD calculated above using the equation:

$$WI = \frac{CV}{\sqrt{RD}}$$

The effective composition concept can be used with other standard methods to calculate such properties as compressibility, density, etc.

Figure 3:
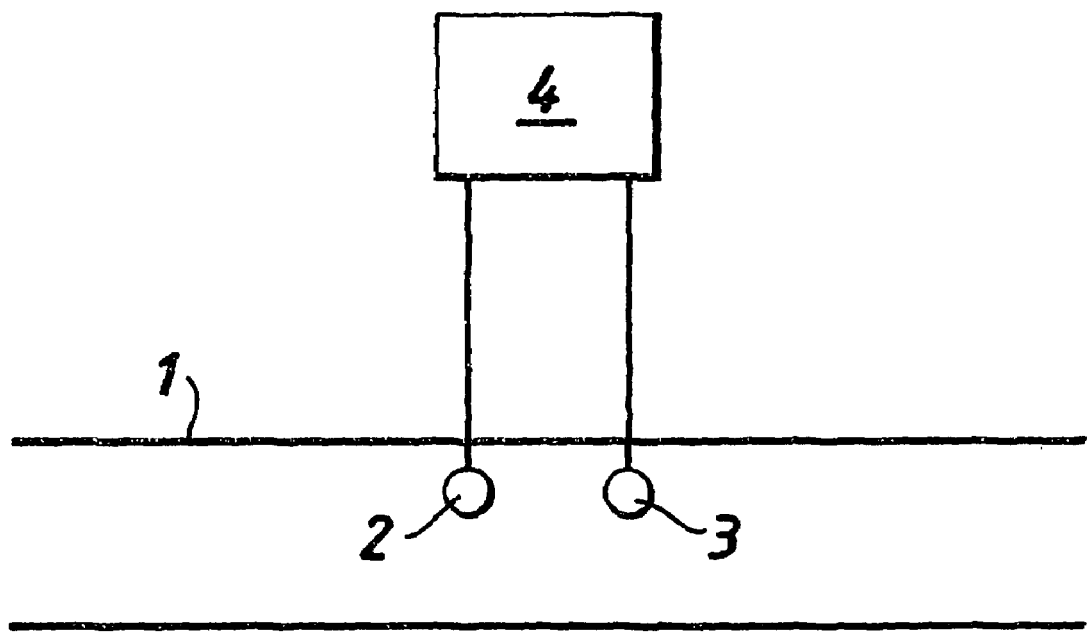
FIG. 3 shows an apparatus for performing the invention.

The invention may be performed by an apparatus using an appropriate number of sensors or detectors, in this case a thermal conductivity detector arranged to measure the thermal conductivity of a gas at two temperatures and a speed of sound detector; and a control means to perform the appropriate processing which could be a computer for example. Such an apparatus is shown in FIG. 3. A fluid in this case, natural gas, is supplied in a conduit 1. A thermal conductivity sensor 2 having means to measure the thermal conductivity of the natural gas at two different temperatures is provided in the conduit. A device 3 to measure the speed of sound of the natural gas is also provided. The thermal conductivity sensor 2 and the speed of sound sensor 3 are both connected to a control means 4, in this case a computer to receive signals indicative of the thermal conductivity of the passing natural gas at two different temperatures and the speed of sound of the passing natural gas to determine the effective composition of the passing natural gas. The control means 4 may also use the determined effective composition to calculate a quantity indicative of the quality of the gas.

The method of the invention may be provided on a digital storage media such as a CD-ROM for installation on a suitable apparatus such as a computer connected to appropriate sensors on detectors.

What is claimed is:

1. A method for determining the effective composition of a gas mixture which contains a plurality of hydrocarbon gases, comprising:
    selecting one or more effective hydrocarbons to represent the plurality of hydrocarbon gases in the gas mixture, the number of effective hydrocarbons being less than the number of hydrocarbon gases in the gas mixture whose composition is to be determined;
    measuring a number of characteristics of the gas mixture whose effective composition is to be determined, wherein the number of characteristics to be measured is one less than the total number of components to be determined and
    determining the effective composition of the mixture of gases from (a) the measurements of the characteristics of the gas mixture, (b) a predetermined parameter dependent upon the characteristic measured, and (c) knowing that the sum of the components of the gas mixture equals 100%,
    wherein said gas mixture includes carbon dioxide and nitrogen in addition to a plurality of hydrocarbon gases and
    wherein the gas characteristics that are measured are thermal conductivity at a first temperature, thermal conductivity at a second temperature and the speed of sound in the gas.

2. A method for determining the proportion of different gases in a gas mixture which contains a plurality of hydrocarbon gases, comprising:
    selecting one effective hydrocarbon or two or more effective hydrocarbons to represent the plurality of hydrocarbon gases in the gas mixture, wherein the number of effective hydrocarbon(s) is fewer than the number of hydrocarbon gases in the gas mixture whose composition is to be determined thus representing said gas mixture as a mixture of the effective hydrocarbon gas(es) and any non-hydrocarbon gas components;

measuring at least one characteristic of the effective gas mixture, wherein the number of different characteristics measured is one fewer than that number of components in the effective gas mixture; and determining the proportion of gases in the effective gas mixture from (a) the measurements of the characteristics of the effective gas mixture, (b) a predetermined parameter dependent upon the characteristic(s) measured, and (c) knowing that the sum of the components of the effective gas mixture equals 100%.

3. The method of claim 2, wherein the hydrocarbon gases in the gas mixture are represented by an effective gas mixture of methane or propane, or methane and propane.

4. The method of claim 2, wherein the gas mixture contains a plurality of hydrocarbon gases, carbon dioxide and nitrogen.

5. The method of claim 2, wherein the amount of a hydrocarbon gas in said hydrocarbon gas mixture is represented by an effective amount of methane, propane, or methane and propane determined from the table below:

| Hydrocarbon gas | Effective amount of methane | Effective amount of propane |
| --- | --- | --- |
| Methane | 1.0 | |
| Ethane | 0.5 | 0.5 |
| Propane | | 1.0 |
| Butane | −0.5 | 1.5 |
| Pentane | −1.0 | 2.0 |
| Hexane | −1.5 | 2.5 |

6. The method of claim 2, wherein the gas mixture contains a plurality of hydrocarbon gases represented by an effective gas mixture of methane and propane, nitrogen and carbon dioxide, and wherein three different characteristics of the gas mixture are measured to determine the proportions of the four different gas components of the effective gas mixture which are carbon dioxide, nitrogen, and the two effective gas components methane and propane.

7. The method of claim 6, wherein the three different characteristics of the gas mixture which are measured are thermal conductivity at a first temperature, thermal conductivity at a second temperature, and the speed of sound in the natural gas mixture.

8. The method of claim 2, further comprising determining the calorific value from the effective proportions of gases in the gas mixture.

9. The method of claim 2, further comprising determining the relative density from the effective proportions of gases in the gas mixture.

10. The method of claim 2, further comprising determining the Wobbe index from the effective proportions of gases in the gas mixture.

11. A method for determining the proportion of different gases in a gas mixture which contains N different hydrocarbon gases, wherein $N \geq 2$ comprising:

selecting $N_{effective}$ hydrocarbon(s) to represent the N different hydrocarbons in said gas mixture, wherein $N_{effective} < N$, thus representing the N different hydrocarbon gases in said gas mixture as a less complex mixture of $N_{effective}$ hydrocarbon gases;

measuring $N_{effective}-1$ characteristics of the gas mixture;

determining the proportion of effective gases in the gas mixture from (a) the measurements of the characteristics of the effective gas mixture, (b) a predetermined parameter dependent upon the characteristic(s) measured, and (c) knowing that the sum of the effective hydrocarbon gas components and any non-hydrocarbon gases in the gas mixture equals 100%.

12. The method of claim 11, wherein $N_{effective}=1$.

13. The method of claim 11, wherein $N_{effective}=2$.

14. The method of claim 11, wherein $N_{effective}=2$ and the two effective gases are methane and propane.

15. The method of claim 11, wherein $N_{effective}=2$ and at least one of the effective gases is a gas other than methane or propane.

16. The method of claim 11, wherein the effective gas mixture has four effective components: the two effective gases, carbon dioxide and nitrogen.

17. The method of claim 11, wherein measuring $N_{effective}-1$ characteristics of the gas mixture comprises at least one measurement selected from the group consisting of the thermal conductivity of the gas at a first temperature, the thermal conductivity of a gas a second temperature, and the speed of sound in the gas.

18. The method of claim 11, further comprising determining the calorific value, relative density or Wobbe index from the effective proportions of gases in the gas mixture.

19. An apparatus for determining the effective composition of a mixture of gases including a plurality of hydrocarbon gases, the apparatus comprising:

control means for selecting one or more effective hydrocarbon component(s) to represent the plurality of hydrocarbon gases in the gas mixture, the number of effective hydrocarbons being less than the number of hydrocarbon gases in the gas mixture whose composition is to be determined;

measuring means for measuring a number of characteristics of the gas mixture whose effective composition is to be determined, the number of characteristics to be measured by the measuring means being one less than the total number of components to be determined and determining the effective composition of the mixture of gases from the measurements of the characteristics of the gas mixture, a predetermined parameter dependent upon the characteristic measured and knowing that the sum of the components of the gas mixture equals 100%.

20. The apparatus of claim 19, wherein said effective gas mixture comprises at least two effective hydrocarbon gases, carbon dioxide and nitrogen.

21. The apparatus of claim 19, wherein said measuring means comprise means for measuring at least one characteristic of the gas mixture selected from the group consisting of thermal conductivity at a first temperature, thermal conductivity at a second temperature, and the speed of sound in the gas mixture.

* * * * *